United States Patent
Li et al.

(10) Patent No.: US 7,081,211 B2
(45) Date of Patent: Jul. 25, 2006

(54) MULTI-LAYER REACTION MIXTURES AND APPARATUSES FOR DELIVERING A VOLATILE COMPONENT VIA A CONTROLLED EXOTHERMIC REACTION

(75) Inventors: Yu-jun Li, Kobe (JP); Mark Hsiang-Kuen Mao, Kobe (JP); Haruo Tamura, Kobe (JP); Hsin-Yuan Hu, Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 481 days.

(21) Appl. No.: 10/340,993

(22) Filed: Jan. 13, 2003

(65) Prior Publication Data

US 2003/0105192 A1    Jun. 5, 2003

Related U.S. Application Data

(63) Continuation of application No. PCT/US00/19081, filed on Jul. 13, 2000.

(51) Int. Cl.
C09K 5/16 (2006.01)
C09K 5/18 (2006.01)
C09K 3/18 (2006.01)
F24J 1/00 (2006.01)
A61K 8/02 (2006.01)

(52) U.S. Cl. ............. 252/70; 252/183.12; 252/183.13; 252/183.14; 126/263.05; 126/263.06; 512/1

(58) Field of Classification Search .................. 252/70, 252/183.12
See application file for complete search history.

(56) References Cited

U.S. PATENT DOCUMENTS

| 3,374,742 | A |   | 3/1968  | Brite              |
| 3,378,333 | A | * | 4/1968  | Brite ......... 422/236 |
| 3,535,246 | A | * | 10/1970 | Crowell, Jr. .... 252/182.32 |
| 3,903,011 | A |   | 9/1975  | Donnelly           |
| 4,913,168 | A |   | 4/1990  | Potter et al.      |
| 5,238,915 | A |   | 8/1993  | Fuwa et al.        |
| 5,935,486 | A |   | 8/1999  | Bell et al.        |

(Continued)

FOREIGN PATENT DOCUMENTS

FR    2 065 782 A    8/1971

(Continued)

*Primary Examiner*—Joseph D. Anthony
(74) *Attorney, Agent, or Firm*—Brent M. Peebles; Angela M. Stone; Kim William Zerby (57) ABSTRACT

Multi-layer reaction mixtures that includes exothermic generating particles having a water soluble coating encasing a portion of the particles, a volatile component and, optionally, a buffer, an aqueous solution or both. At least two layers of the reaction mixture contain exothermic generating particles and at least one layer of the reaction mixture contains a portion of the exothermic generating particles suspended in a gel that includes the water soluble coating. These multi-layer reaction mixtures are especially suited to generate heat in a controllable manner. In one such controlled reaction, the reaction components are mixed together and the reaction mixture increases in temperature to a Set Temperature within a predetermined time, and the mixture remains at the Set Temperature for a longer period of time. In this manner, volatile components can be controllably released to the surrounding environment. The volatile components can be, for example, a perfume, a fragrance, an insect repellent, a fumigant, a disinfectant, a bactericide, an insecticide, a pesticide, a germicide, an acaricide, a sterilizer, a deodorizer, a fogging agent and mixtures of these. Apparatuses and methods that use these multi-layer reaction mixtures are also disclosed.

21 Claims, 4 Drawing Sheets

U.S. PATENT DOCUMENTS

| | | |
|---|---|---|
| 5,993,854 A | 11/1999 | Needleman et al. |
| 6,099,556 A * | 8/2000 | Usui .......................... 607/114 |
| 6,180,124 B1 * | 1/2001 | Ohta et al. ................. 424/401 |
| 6,289,889 B1 * | 9/2001 | Bell et al. .............. 126/263.07 |
| 6,436,128 B1 * | 8/2002 | Usui .......................... 607/96 |

FOREIGN PATENT DOCUMENTS

| | | |
|---|---|---|
| JP | 2200626 A2 | 8/1990 |
| JP | 6134025 A2 | 5/1994 |
| JP | 9220045 | 11/1995 |
| JP | 8131869 A2 | 5/1996 |
| JP | 63260566 | 10/1998 |
| JP | 10298016 A2 | 11/1998 |
| JP | 11286429 A2 | 10/1999 |
| JP | 11286431 A2 | 10/1999 |
| WO | WO 99/48469 | 9/1999 |

* cited by examiner

MULTI-LAYER REACTION MIXTURES AND APPARATUSES FOR DELIVERING A VOLATILE COMPONENT VIA A CONTROLLED EXOTHERMIC REACTION

CROSS REFERENCE TO PRIOR APPLICATION

This is a continuation of International Application PCT/US00/19081, with an international filing date of Jul. 13, 2000, published in English.

TECHNICAL FIELD

The present invention relates to multi-layer reaction mixtures that include exothermic generating particles having a water soluble coating encasing a portion of the particles, an aqueous solution, a volatile component, and, optionally, a buffer. The multi-layer reaction mixtures are especially suited to generate heat in a controllable manner. Volatile components can be controllably released to the surrounding environment by the present multi-layer reaction mixtures. Apparatuses and methods that use these multi-layer reaction mixtures are also disclosed.

BACKGROUND OF THE INVENTION

There are many methods for delivering airborne components, such as fragrances, insect repellents and the like. Scented candles, for example, are well know implements for delivering a desirable smell to the air. Incense performs essentially the same function, but the aroma is typically the natural smell evolved when the incense is burned. That is, incense typically does not require the addition of a fragrant component, while scented candles are generally a mixture of wax and a fragrance. In yet another variant of aroma delivering combustion devices, candles have been used to heat liquids or gels causing a volatile component to, evolve. Moreover, lamps that burn oil have been used for ages, not only to provide light, but also to deliver fragrances. Combustion devices for delivering fragrances are well know, but most of these devices have also been used to deliver other airborne components, such as insect repellents, medicinal vapors such as eucalyptus, and other compounds.

Unfortunately, combustion devices inherently give rise to safety issues. They can be accidentally knocked over resulting in a fire, or when left unattended, many combustion devices can burn down to their base and ignite the surrounding surface. Moreover, smoke is an inevitable by-product of any combustion device. In general, smoke from a combustion device can be noxious, and may cause long term health problems. Thus, while these devices are simple and inexpensive methods for delivering airborne components, they are not without problems.

Another method of delivering airborne components is to simply rely on evaporation. For example, a liquid, solid or gel material that contains an airborne component can be placed anywhere and over time the airborne component will evolve to the surrounding environment via evaporation. But this system relies on the difference between the vapor pressure of the airborne component and atmospheric pressure. If the vapor pressure of the airborne component is too high, the component will be delivered to fast. Likewise, if the vapor pressure of the component is too low, the component will be delivered too slowly to make a marked effect in the surrounding environment. Many insect repellents, for example, cannot be delivered effectively by evaporation alone because of their high vapor pressure. Thus, evaporative devices are very limited in the type of material they can deliver, and the speed with which these select materials can be delivered.

Slightly more advanced apparatuses for delivering airborne components use electrical power from batteries or an electrical outlet in the home. These devices typically use the electricity to provide heat, forced air flow, or both to speed the delivery of the airborne component. Unfortunately, these devices are necessarily more complicated and expensive to build and operate than are combustion and evaporative devices. While these devices may improve delivery, they increase complexity and cost. Moreover, the devices that are not battery operated are inherently not portable as they require an electrical outlet.

Sprays and aerosols can deliver a wide variety of materials to the air. But these devices are, in general, manually operated and provide a short burst of the delivered component. Sprays and aerosols are not well suited for the prolonged delivery of a substance unless they are provided with a mechanical control mechanism. Such mechanical controls are expensive and limit the portability of such devices.

Self contained exothermic reaction mixtures that are initiated with an aqueous solution have been considered for delivering compositions to the surrounding air. A self contained exothermic reaction can provide heat without a combustion or an electrical source. The heat, in turn, can speed the evaporation of the composition that one wishes to deliver. As such, a wider range a compositions can be delivered in this manner. But these reactions have one substantial problem, they are hard to control. For example, it has been difficult to design a reaction system that is self contained, and runs at a constant temperature for an extended period of time. Likewise, it is difficult to design a reaction system that will run at one temperature for a first period of time, then change to a second temperature for a second period of time. It is axiomatic that one cannot control the delivery of the desired composition without controlling the temperature of the reaction system.

Thus, there exists a need for improved methods and apparatuses for delivering compositions to the surrounding air. These improved methods and apparatuses should overcome the problems discussed above. Specifically, they should not require combustion, and they should not rely solely on evaporation. There is a need for devices that deliver compositions to the air in a more controlled manner and for a longer period of time than aerosols and sprays. Moreover, these improved methods and apparatuses should be portable and relatively inexpensive.

SUMMARY OF THE INVENTION

The present invention is directed to a multi-layer reaction mixture comprising the following reaction components: exothermic generating particles comprising a water soluble coating that encases a portion of the particles; and a volatile component. Optionally, the reaction components further comprise additional reactants selected from the group consisting of a buffer, an aqueous solution, and mixtures thereof. At least two layers of the reaction mixture comprise exothermic generating particles and at least one layer of the reaction mixture comprises a portion of the exothermic generating particles suspended in a gel comprising the water soluble coating.

In one aspect of this invention the reaction components are mixed together, and the temperature of the reaction mixture increases to a Set Temperature that is greater than about 35° C. and less than about 75° C. within less than about 20 minutes. More preferably, the reaction mixture remains within 15° C. of the Set Temperature for at least about 45 minutes.

The exothermic generating particles of the present invention are preferably selected from the group consisting of uncomplexed metals, metal salts, metal oxides, metal hydroxides, metal hydrides and mixtures thereof. The metals are selected from the group consisting of beryllium, magnesium, lithium, sodium, calcium, potassium, iron, copper, zinc, aluminum and mixtures thereof. And the water soluble coating for these exothermic generating particles comprises a water soluble material preferably selected from the group consisting of natural water-soluble polymers, inorganic water-soluble polymers, synthetic water-soluble polymers, semi-synthetic water-soluble polymers, polymers of plant origin, polymers of microorganism origin, polymers of animal origin, starch polymers, cellulose polymers, alginate polymers, vinyl polymers, polyoxyethylene polymers, acrylate polymers, and mixtures thereof.

In yet another aspect of this invention there is provided an apparatus for generating heat comprising a multi-layer reaction mixture comprising the following reaction components: exothermic generating particles comprising a water soluble coating that encases a portion of the particles; and a volatile component. At least two layers of the reaction mixture comprise exothermic generating particles and at least one layer of the reaction mixture comprises a portion of the exothermic generating particles suspended in a gel comprising the water soluble coating. Optionally, the reaction components further comprise additional reactants selected from the group consisting of a buffer, an aqueous solution, and mixtures thereof.

The methods and apparatuses of this invention provide portable and inexpensive ways to deliver compositions to the surrounding air in a controllable manner. The devices can be relatively small while operating in a controllable manner for an extended period of time. For example, a multi-layer reaction mixture can be designed to deliver a component to the surrounding environment for an extended period of time at a relatively controlled rate. Moreover, using the multi-layer reaction mixtures of the present invention a first component can be delivered to the air for a first period of time, then the reaction mixture can automatically change temperature to deliver a second component for a second period of time.

The apparatuses of this invention can be used to deliver a variety of useful compounds to the surrounding air, and to clothes, carpet, pets, skin and many other surfaces. Moreover, the apparatuses of this invention can be combined with color and light to improved the aesthetic qualities, and ultimately, improve the overall experience for the user of the apparatus.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings in which:

DETAILED DESCRIPTION OF THE INVENTION

As noted, the present invention is directed to a multi-layer reaction mixture comprising the following reaction components: exothermic generating particles comprising a water soluble coating that encases a portion of the particles; a volatile component; and an aqueous solution. Optionally, the reaction components further comprise a buffer. At least two layers of the reaction mixture comprise exothermic generating particles and at least one layer of the reaction mixture comprises a portion of the exothermic generating particles suspended in a gel formed by the water soluble coating. The multi-layer reaction mixture can be used to generate heat in a controllable manner, which, in turn, assists in the evolution of the volatile component in a controlled manner. Apparatuses that utilize the multi-layer reaction mixtures taught herein are also disclosed.

Multi-Layer Reaction Mixture

In one aspect of this invention a reaction mixture is formed by mixing the reaction components to initiate an exothermic reaction between the exothermic generating particles and the aqueous solution. The exothermic reaction generates heat, which elevates the temperature of the multi-layer reaction mixture. The heat, more precisely, the elevated temperature of the multi-layer reaction mixture, aides the evolution of the volatile component from the multi-layer reaction mixture. As will be understood, the water soluble coating of the exothermic generating particles can be used to control the speed of the exothermic reaction, and the heat generated. The ability to control the amount of heat generated by the multi-layer reaction mixture, without any external controls, allows for the controlled delivery of the volatile component.

It has been found that suspending a potion of the exothermic generating particles in a multi-layered gel provides a method for achieving the desired temperature control of the exothermic reaction. The different layers can be designed to control the rate of the exothermic reaction, deliver different volatile components, provide different exothermic generating particles, provide different water soluble coatings, provide pleasing aesthetics, or combinations of these.

Figure 1:
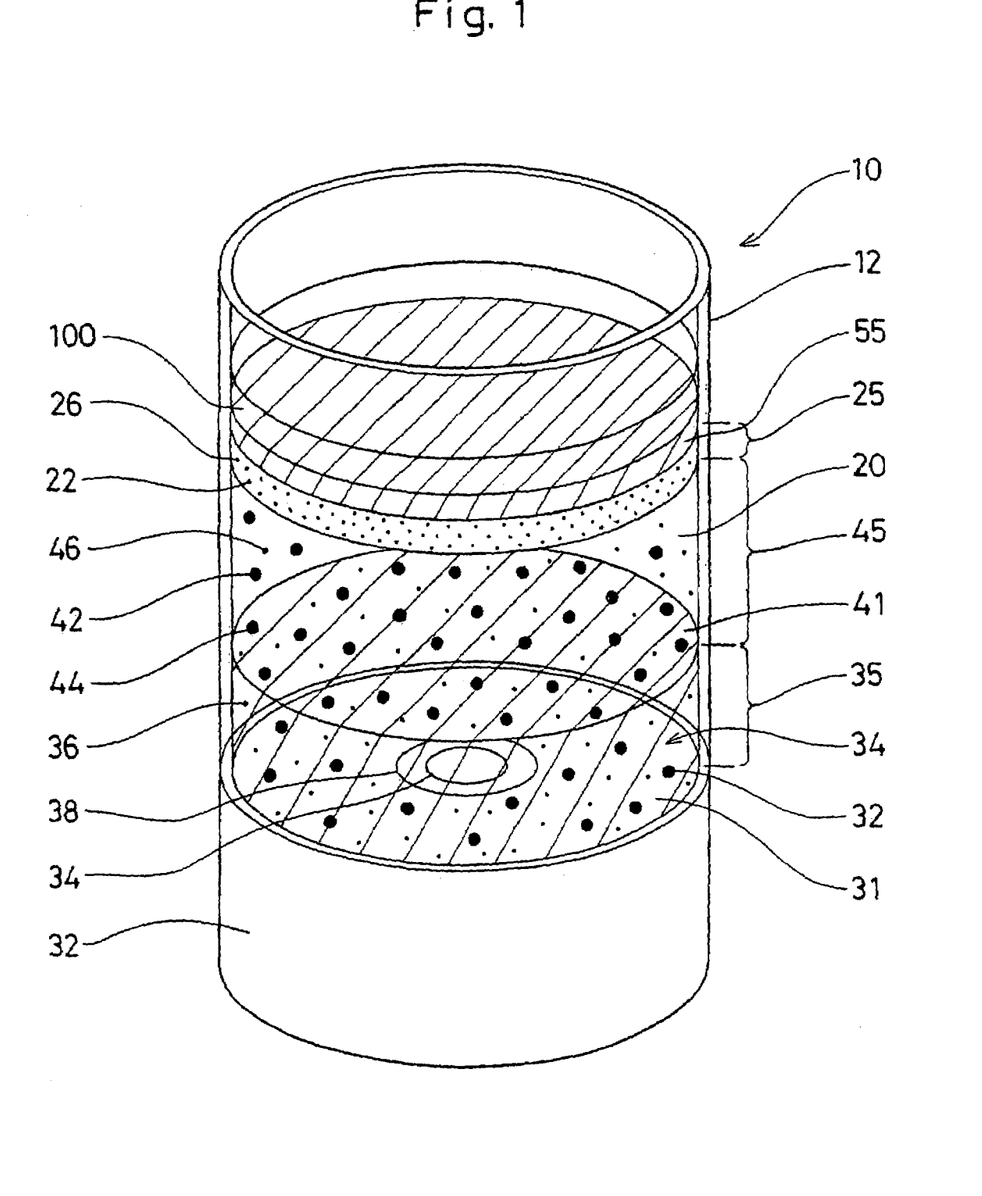
FIG. 1 is a schematic representation of an apparatus comprising a multi-layer reaction mixture of the present invention.

FIG. 1 illustrates a schematic representation of an apparatus 10 comprising a multi-layer reaction mixture 20 of the present invention. Apparatus 10 comprises container 12 and multi-layer reaction mixture 20, which includes: exothermic generating particles 22 in layer 25; exothermic generating particles 32 with coating 34 in layer 35; exothermic generating particles 42 with coating 44 in layer 45; and layer 55. Multi-layer reaction mixture 20 further comprises buffer particles 26, 36 and 46 and an aqueous solution 100. Volatile components 31 and 41 are dispersed in layer 35 and 45, respectively. The volatile components 31 and 41 can be incorporated into coatings 34 and 44, or alternatively, volatile components 34 and 44 can be suspended in layers 35 and 45 as emulsified droplets. Multi-layered reaction mixture 20 is shown in container 12 that sits on base 32 that houses light source 34 and power source 38.

As shown in FIG. 1, layer 55 is substantially free of exothermic generating particles, and in layer 25 of multi-layered reaction mixture 20 the exothermic generating particles are in the form of a dry powder, that is, with essentially no coating. Moreover, volatile components 31 and 41 in layers 35 and 45 respectively, can be different compositions, although this need not be the case.

Figure 2:
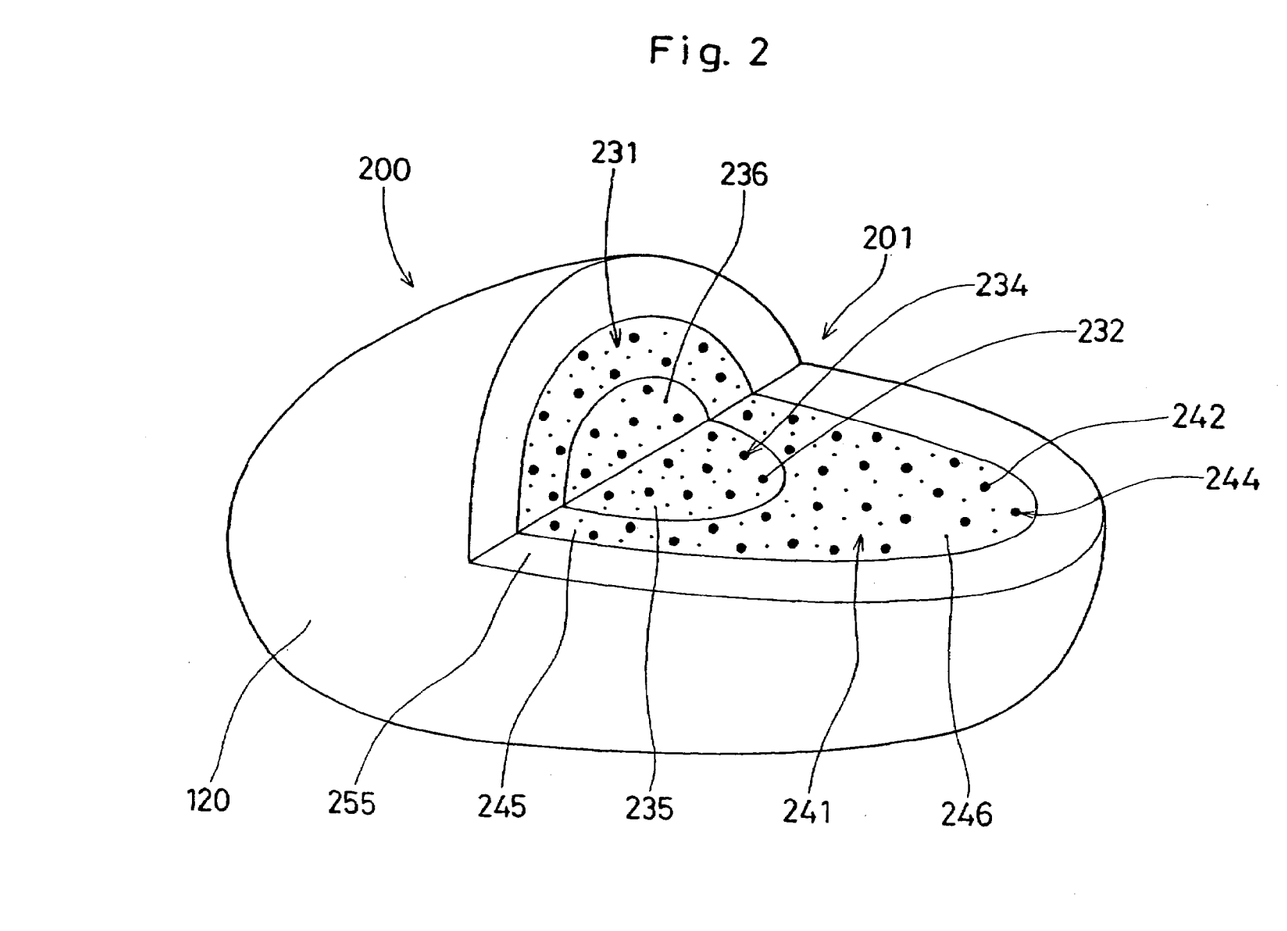
FIG. 2 is a schematic representation of a multi-layer reaction mixture according to the present invention in the form of a self contained capsule.

FIG. 2 is a schematic representation of a multi-layer reaction mixture 120 according to the present invention in the form of a self contained capsule 200. Cut-away section 201 of capsule 200 shows three different layers 235, 245 and 255. Capsule 200 contains exothermic generating particles exothermic 232 with coating 234 in layer 235; and exothermic generating particles 242 with coating 244 in layer 245. Multi-layer reaction mixture 120 further comprises buffer particles 236 and 246. Volatile components 231 and 241 are dispersed in layer 235 and 245, respectively. The volatile components 231 and 241 can be incorporated into coatings 234 and 244, or alternatively, volatile components 234 and 244 can be suspended in layers 235 and 245 as emulsified dropplets. To initiate the desired exothermic reaction, capsule 200 is mixed with an aqueous solution (not shown). This mixing can be accomplished in any appropriate container.

Figure 3:
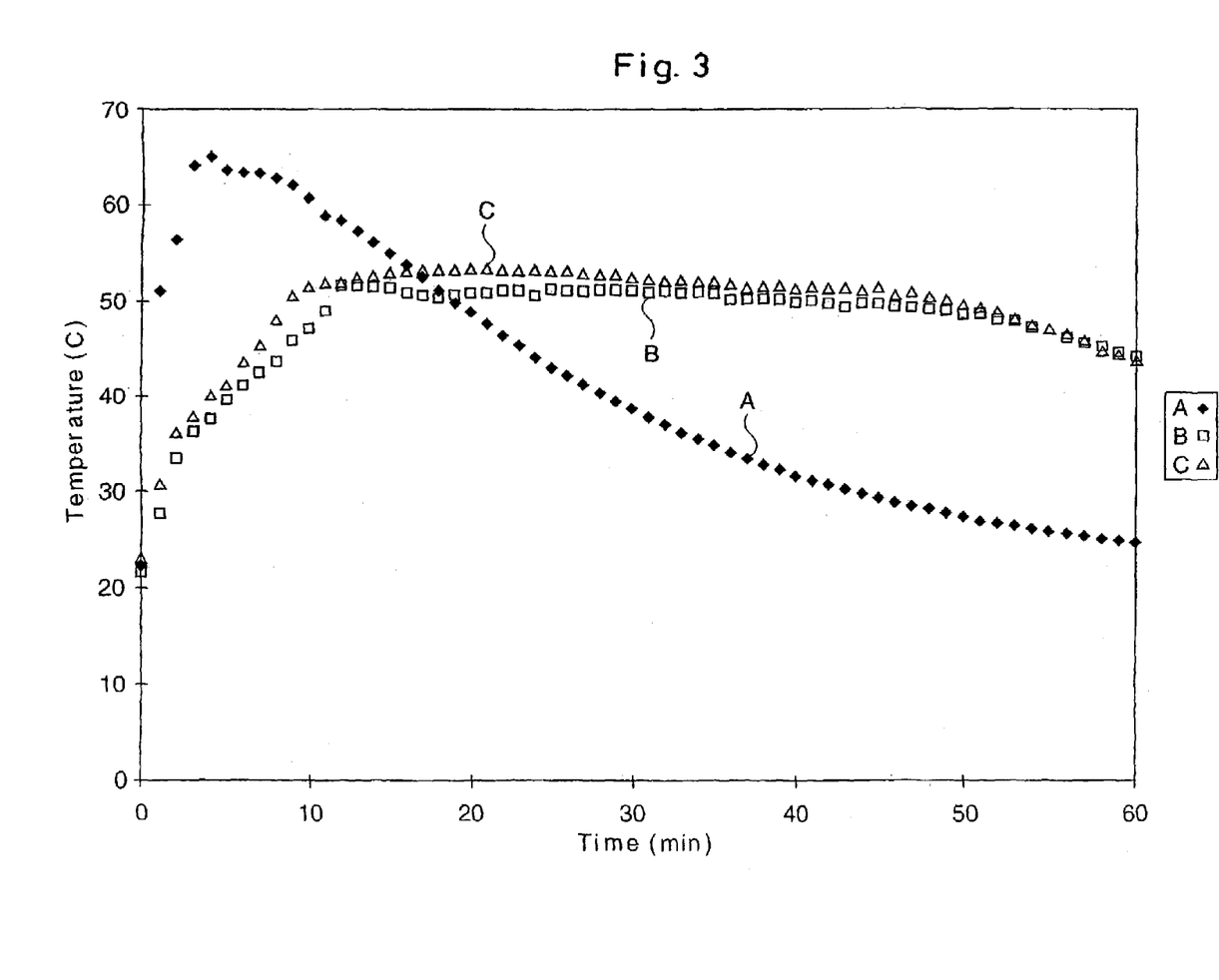
FIG. 3 is a graphical representation of two controlled reactions with a Set Temperature of about 50° C. using multi-layer reaction mixtures according to the present invention, and an uncontrolled reaction.
Figure 4:
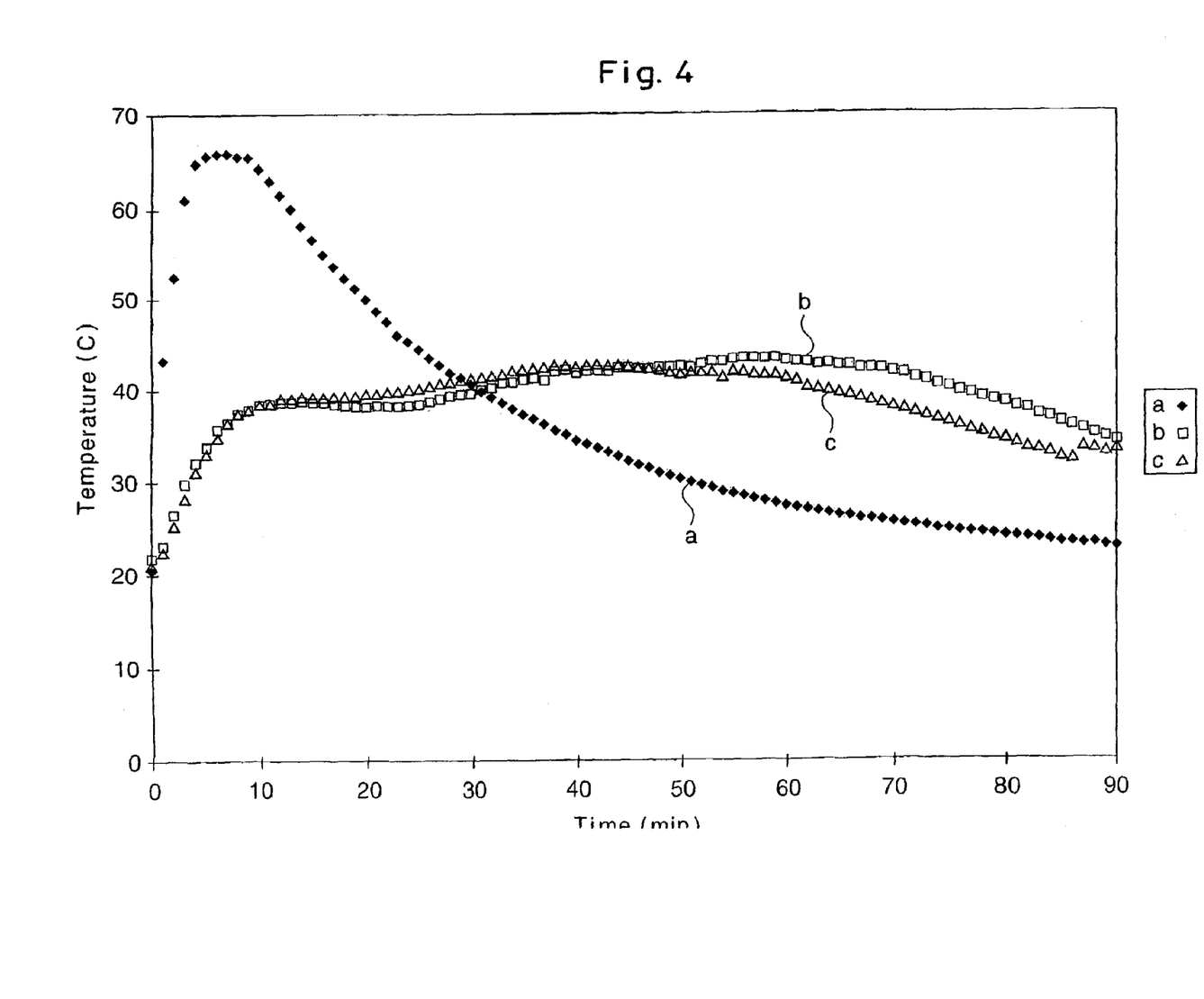
FIG. 4 is a graphical representation of two controlled reactions with a Set Temperature of about 40° C. using multi-layer reaction mixtures according to the present invention, and an uncontrolled reaction.

As discussed above, the purpose of the water soluble coatings used in the multi-layered reaction products disclosed herein, is to control the rate of the exothermic reaction. As is well known to those skilled in the art, chemical reactions can be difficult to control. Assuming a batch process, and putting aside thermodynamic considerations, the rate of an exothermic chemical reaction depends largely on the temperature and concentration of the multi-layer reaction mixture. With no external controls, the temperature of an exothermic reaction mixture will rapidly increase during the early stages of the reaction. This is due largely to two factors, the concentration of the reactants is at its highest level, and as the reaction progresses heat is generated which raises the temperature of the reaction mixture, which, in turn, increases the rate of the reaction. As the reactants are depleted, the reaction slows, causing a precipitous decrease in the temperature of the reaction mixture. This effect if graphically illustrated in both FIGS. 3 and 4, specifically, lines "A" and "a" illustrate the temperature of an uncontrolled exothermic reaction mixture as a function of time. FIGS. 3 and 4 are discussed in greater detail below, but they clearly illustrate one problem addressed by the present invention. That is, the temperature of the reactions represented by Lines "A" and "a" of FIGS. 3 and 4, respectively, changes constantly. Moreover, the rate of change of the temperature is almost never constant.

By coating the exothermic generating particles as described in detail below, multi-layer exothermic reaction mixture can be designed to provide constant heat over relatively long periods of time. And other control schemes can be easily designed by those skilled in the art, for example, a multi-layer reaction mixture can be designed where the temperature increases gradually at a constant rate of increase for a relatively long period of time. Other control schemes will be apparent based on the following details.

In one such control scheme, a multi-layer reaction mixture is prepared by mixing the reaction components to initiate an exothermic reaction. The temperature of the reaction mixture increases to a Set Temperature that is greater than about 35° C. and less than about 75° C., preferably between about 35° C. and 60° C., and most preferably between about 35° C. and 50° C., within less than about 20 minutes, preferably within less than about 10 minutes and more preferably within less than about 5 minutes. Preferably, the reaction mixture remains within 15° C., more preferably within 10° C., and even more preferably within 5° C. of the Set Temperature for at least about 45 minutes, preferably at least about 60 minutes, and more preferably at least about 90 minutes. It is understood that the term "remains within" as used herein, means the same as "±". For example, to "remain within 10° C." of a Set Temperature of 50° C., means the temperature can fluctuate between 40° C. and 60° C. This control scheme is graphically illustrated in FIGS. 3 and 4 by Lines "B", "C", "b" and "c".

FIG. 3 displays one "uncontrolled" exothermic reaction according to the prior art ("A") compared to two "controlled" reactions according to the present invention ("B" and "C"). The reaction components, and the resulting multi-layer reaction mixture are given in Table 1 and summarized in Table 2. As can be seen, magnesium powder is used as the exothermic generating particles, and a citric acid buffer is used. The exothermic generating particles of reaction mixture "A" are uncoated (Premix 2), while the exothermic generating particles of multi-layer reaction mixtures "B" and "C" include both uncoated particles (Premix 2), and particles coated with Polyethylene Glycol ("PEG") of different molecular weights (Premix 1). The weight of the reactants (excluding the coating material) was held constant in these three reaction mixtures. That is, the weight of the magnesium exothermic generating particles and the citric acid buffer was held relatively constant in all three reaction mixtures, see Table 2. Moreover, the magnesium exothermic generating particles and the citric acid buffer was added to 100.0 grams of water to form each of the reaction mixtures.

TABLE 1

| INGREDIENT | A Wt. % | B Wt. % | C Wt. % |
|---|---|---|---|
| Premix 1 | | | |
| PEG 600 | 0.0 | 15.0 | 13.5 |
| PEG1000 | 0.0 | 5.0 | 4.5 |
| Magnesium | 0.0 | 5.0 | 4.5 |
| Citric acid | 0.0 | 32.5 | 29.3 |
| Premix 2 | | | |
| Magnesium | 13.3 | 5.7 | 6.4 |
| Citric acid | 86.7 | 36.8 | 41.8 |
| Total Wt. % | 100 | 100 | 100 |

TABLE 2

| INGREDIENT | A Wt. (g) | B Wt. (g) | C Wt. (g) |
|---|---|---|---|
| Coating | 0.0 | 4.8 | 4.3 |
| Mg | 2.6 | 2.6 | 2.6 |
| Citric Acid | 16.6 | 16.6 | 17.1 |
| Water | | | |
| Total Wt. (g) | 19.2 | 24.0 | 24.0 |

As discussed briefly above, Line "A" is a typical graph of temperature v. time for an uncontrolled exothermic reaction. The temperature rises rapidly at first to a maximum of greater than 65° C. And then, as the reaction components are consumed, the temperature begins to decrease along a logarithmic curve. And within approximately 35 minutes, the reaction has cooled to within 5° C. of the initial temperature (room temperature). At no time during this first 35 minutes of the reaction illustrated by Line "A" does the temperature remain constant for more than a few minutes.

In sharp contrast, the multi-layer reaction mixtures represented by lines "B" and "C" of FIG. 3, increase to the Set Temperature of about 50° C. within about 10 minutes. The reaction temperatures then level off and remain within 5° C. of the Set Temperature for at least about 45 minutes.

Similarly, FIG. 4 displays one "uncontrolled" exothermic reaction according to the prior art ("a") compared to two "controlled" reactions according to the present invention ("b" and "c"). The reaction components, and the resulting reaction mixture are given in Table 3 and summarized in Table 4. Magnesium powder is used as the exothermic generating particles, and a citric acid buffer is used. The exothermic generating particles of reaction mixture "a" are uncoated (Premix 2), while the exothermic generating particles of multi-layer reaction mixtures "b" and "c" include both uncoated particles (Premix 2), and particles coated with Polyethylene Glycol ("PEG") of different molecular weights (Premix 1). The weight of the reactants (excluding the coating material) was held constant in these three reaction mixtures. That is weight of the magnesium exothermic generating particles and the citric acid buffer was held relatively constant in all three reaction mixtures, see Table 4. Moreover, the magnesium exothermic generating particles and the citric acid buffer was added to 100.0 grams of water to form each of the reaction mixtures.

TABLE 3

| INGREDIENT | a Wt. % | b Wt. % | c Wt. % |
|---|---|---|---|
| Premix 1 | | | |
| PEG 600 | 0.0 | 13.0 | 13.4 |
| PEG 1000 | 0.0 | 21.3 | 22.0 |
| PEG 2000 | 0.0 | 7.1 | 7.3 |
| Magnesium | 0.0 | 5.0 | 4.7 |
| Citric acid | 0.0 | 32.3 | 30.5 |
| Premix 2 | | | |
| Magnesium | 13.3 | 2.8 | 2.9 |
| Citric acid | 86.7 | 18.5 | 19.0 |
| Total Wt. % | 100 | 100 | 100 |

TABLE 4

| INGREDIENT | a Wt. (g) | b Wt. (g) | c Wt. (g) |
|---|---|---|---|
| Coating | 0.0 | 10.5 | 10.4 |
| Mg | 2.0 | 2.0 | 1.9 |
| Citric Acid | 12.9 | 12.9 | 12.2 |
| Total Wt. (g) | 14.9 | 25.4 | 24.5 |

As discussed briefly above, Line "a" is a typical graph of temperature v. time for an uncontrolled exothermic reaction. The temperature rises rapidly at first, and then as the reaction components are consumed, the temperature begins to decrease along a logarithmic curve. It takes approximately 15 minutes for the temperature of reaction mixture "a" to overshoot and cool back down to 55° C., which is within 15° C. of the Set temperature, 40° C. The reaction mixture remains within 15° C. of 40° C. for only about 40 minutes later when the reaction dips below 25° C. At no time during this first 55 minutes of the reaction illustrated by Line "a" does the temperature remain constant for more than a few minutes.

In sharp contrast, the multi-layer reaction mixtures represented by lines "b" and "c" of FIG. 4, increase to the Set Temperature of about 40° C. within about 10 minutes. The reaction temperatures then level off and remain within 5° C. of the Set Temperature for at least about 60 minutes.

It is understood that the control scheme depicted in FIGS. 3 and 4, that is, where the reaction mixture rises to a Set Temperature and the temperature remains relatively constant for an extended period of time, is only one of many possible control schemes covered by the present invention. By way of example, another control scheme occurs when the reaction components are mixed together, the temperature of the reaction mixture increases to a First Set Temperature and remains within 15° C., preferably within 10° C., and more preferably within 5° C. of the First Set Temperature for a first period of time and then moves to a Second Set Temperature and remains within 15° C., preferably within 10° C., and more preferably within 5° C. of the Second Set Temperature for a second period of time. Preferably, the first period of time is at least about 15 minutes, preferably at least about 20 minutes, and the second period of time is at least about 15 minutes, preferably at least about 20 minutes. And it is also preferred that the First Set Temperature be at least about 10° C., preferably at least about 15° C., greater than the Second Set Temperature, or alternatively, the First Set Temperature is at least about 10° C., preferably at least about 15° C., less than the Second Set Temperature.

Yet another example of a control scheme of the present invention is when the reaction components are mixed together the temperature of the reaction mixture increases at an actual rate of increase that is measured in ° C./minute, and the actual rate of increase remains within 0.5° C./minute, preferably within 0.1° C./minute, and more preferably within 0.01° C./minute of a predetermined rate of increase for at least about 45 minutes, preferably at least about 60 minutes, and more preferably at least about 90 minutes. Preferably the predetermined rate of increase is less than 2° C./minute, preferably less than 1.5° C./minute, and more preferably less than 1° C./minute.

Reaction Components

Turning now to the reaction components, which include as a minimum, exothermic generating particles comprising a water soluble coating that encases a portion of the particles, and a volatile component. Preferably, the reaction components further comprise a buffer, an aqueous solution or both.

Exothermic Generating Particles

The exothermic generating particles of the present invention are preferably selected from the group consisting of uncomplexed metals, metal salts, metal oxides, metal hydroxides, metal hydrides and mixtures thereof. The metals are selected from the group consisting of beryllium, magnesium, lithium, sodium, calcium, potassium, iron, copper, zinc, aluminum and mixtures thereof. These particles may also be selected from the group consisting of beryllium hydroxide, beryllium oxide, beryllium oxide monohydrate, lithium aluminum hydride, calcium oxide, calcium hydride, potassium oxide, magnesium chloride, magnesium sulfate, aluminum bromide, aluminum iodide, sodium tetraborate, sodium phosphate and mixtures thereof. The concentration of the exothermic generating particles in the reaction mixture is from about 3% to about 70%, preferably from about 5% to about 65%, and more preferably from about 8% to about 60%, by weight, of the multi-layer reaction mixture.

It is preferred, although not required, that the exothermic generating particles (without the coating) have an average particle diameter of from about 10 microns to about 1000 microns, preferably from about 100 microns to about 500 microns, more preferably from about 200 microns to about 400 microns. In the present multi-layer reaction mixture, the exothermic generating particles can be in the form of a dry powder, suspended in a homogenous gel, or suspended in a non-aqueous solution.

Water Soluble Coating

Controlling the temperature of the multi-layer reaction mixture as a function of time is one of the objects of this invention, and control is accomplished largely by coating at least a portion of the exothermic generating particles. While not wanting to be bound by any one theory, it is believed that the coated exothermic generating particles cannot react with the aqueous solution until the coating dissolves. As the coating on the exothermic generating particles begins to dissolve, the exposed particles begin to react and generate heat. In light of this mechanism, one can easily see the benefit of using a mixture of exothermic generating particles have different coatings, different thickness of coatings, or both. Likewise, it is often preferred to include a small amount of uncoated exothermic generating particles to help raise the temperature during the early stages of the reaction. The concentration of the water soluble coating material in the multi-layer reaction mixture is from about 3% to about 70%, preferably from about 5% to about 65%, and more preferably from about 8% to about 60%, by weight, of the multi-layer reaction mixture.

Hence, it is understood that while a portion of the exothermic generating particles must be coated with the water soluble coatings disclosed herein, not all of the particles need to be coated. Moreover, some particles may have different thicknesses, and the coatings may be different. More specifically, the exothermic generating particles can be selected from the group consisting of uncoated particles, coated particles and mixtures thereof, preferably, the exothermic generating particles comprise particles selected from the group consisting of uncoated particles, first coated particles, second coated particles and mixtures thereof, wherein the first coated particle differ from the second coated particles in the coating material, the thickness of the coating or both.

The coating for these exothermic generating particles should be a water soluble material that is preferably selected from the group consisting of natural water-soluble polymers, inorganic water-soluble polymers, synthetic water-soluble polymers, semi-synthetic water-soluble polymers, polymers of plant origin, polymers of microorganism origin, polymers of animal origin, starch polymers, cellulose polymers, alginate polymers, vinyl polymers, polyoxyethylene polymers, acrylate polymers, and mixtures thereof. More specifically, the coating for the exothermic generating particles comprises a water soluble material selected from the group consisting of gum arabic, gum tragacanth, galactan, gum guar, carob-seed gum, karaya gum, carrageenan, pectin, agar, quince seed, alge-colloid, starch (from corn, potato, etc), glycyrrhizic acid, gum xanthan, dextran, succin-glucane, pullulan, collagen, casein, albumin, gelatin, carboxy-methyl starch, methyl-hydroxypropyl starch, methyl-cellulose, nitro-cellulose, ethyl-cellulose, methyl-hydroxypropyl-cellulose, hydroxy-ethyl-cellulose, sodium cellulose sulfate, hydroxypropyl-cellulose, sodium carboxy-methyl-cellulose, crystalline cellulose, cellulose powder, sodium alginate, propylene glycol alginate ether, polyvinyl alcohol, poly (vinyl methyl ether), poly-vinyl-pyrrolidone, carboxy-vinyl polymers, alkyl co-polymers of acrylic acid and methacrylic acid, polyethylene glycol having a molecular weight between 200 and 100,000, preferably between 600 and 20,000, co-polymers of polyoxy-ethylene and polyoxy-propylene, sodium poly-acrylate, poly ehtylacrylate, poly acrylamide, polyethylene imine, cation polymers, bentonite, aluminum magnesium silicate, hectorite, silicic anhydride, and mixtures thereof. Preferably, the coating comprises a material selected from the group consisting of water-soluble alkylene glycols, water-soluble alcohols, and mixtures thereof. Exemplary coatings useful in the present invention are listed below in Table 5.

TABLE 5

| Examples of natural water-soluble polymers | Examples of semi-synthetic water-soluble polymers |
| --- | --- |
| polymers of plant origin | starch-related polymers |
| gum arabic | carboxy-methyl starch |
| gum tragacanth | methyl-hydroxypropyl starch |
| galactan | cellulose-related polymers |
| gum guar | methyl-cellulose |
| carob-seed gum | nitro-cellulose |
| karaya gum | ethyl-cellulose |
| carrageenan | methyl-hydroxypropyl-cellulose |
| pectin | hydroxy-ethyl-cellulose |
| agar | sodium cellulose sulfate |
| quince seed | hydroxypropyl-cellulose |
| alge-colloid | sodium carboxy-methyl- |
| starch (from corn, potato, etc.) | cellulose |
| glycyrrhizic acid | cellulose, crystalline |
| polymers of microorganism origin | cellulose, powder |
| gum xanthan | alginate-related polymers |
| dextran | sodium alginate |
| succin-glucane | propylene glycol alginate ester |
| pullulan | |
| polymers of animal origin | |
| collagen | |
| casein | |
| albumin | |
| gelatin | |
| Examples of synthetic water-soluble polymers | examples of inorganic water-soluble polymers |
| vinyl-related polymers | bentonite |
| polyvinyl alcohol | aluminum magnesium silicate |
| poly (vinyl methyl ether) | Laponite ® |
| poly-vinyl-pyrrolidone | hectorite |
| carboxy-vinyl polymers | silicic anhydride |
| alkyl co-polymers of acrylic acid & methacrylic acid | |
| polyoxyethylene-related polymers | |
| PEG 200 | |
| PEG 600 | |
| PEG 1000 | |
| PEG 2000 | |
| PEG 4000 | |
| PEG 6000 | |
| PEG 20000 | |
| co-polymers of polyoxy-ethylene & polyoxy-propylene | |
| acrylate-related polymers | |
| sodium poly-acrylate | |
| poly ehtylacrylate | |
| poly acrylamide | |
| polyethylene imine | |
| cationic polymers | |

As will be understood by those skilled in the art, the water solubility of the coatings discussed above vary across a broad band. And in general, the water solubility is dependent on temperature. Thus, to control the temperature of a multi-layer reaction mixture a skilled artisan can easily select coatings that dissolve at the desired Set Temperature and vary the thickness of the coatings such that exothermic generating particles are exposed to the aqueous solution at various times. Another method of control is to use different coatings that dissolve at different rates. By this method, certain particles will be exposed early in the reaction, while other exothermic generating particles will take longer to be exposed. Other methods of coating the exothermic generating particles to control an exothermic reaction will be apparent to those skilled in the chemical arts. It is understood that in any control scheme, it may be preferred, although not necessary, to include some particles that are not coated.

The coating can be applied to the exothermic generating particles by any appropriate means. The easiest method is to soften or melt the coating material and mix it with the desired amount of exothermic generating particles. To achieve different coating thicknesses, separate batches of particles and coating materials can be prepared. For example, 100 g of particles can be mixed with 100 g of PEG 600, and separately, 100 g of exothermic generating particles can be mixed with 200 g of PEG 600. The two batches of particles can then be combined. The thickness of the coating can be determined by a simple material balance using the average particle size of the exothermic generating particles and the amount of coating material added thereto. If a more precise measurement is desired, spectroscopic analysis of the particles before and after coating can provide a very accurate particle size distribution. Spectroscopic particle size analyzers are well known.

While it is necessary to coat at least a portion of the exothermic generating particles of the multi-layer reaction mixture, the volatile component, the optional buffer, and the other optional components, (discussed below) may or may not be coated. More specifically, the volatile component, the optional buffer, and the other optional components, can be coated along with the exothermic generating particles, they can be coated separately from the exothermic generating particles, or they can be added without any coating. Combinations of these choices will also produce acceptable results in many cases. Therefore, coating components other than the exothermic generating particles is the prerogative of the formulator.

Volatile Component

The multi-layer reaction mixtures disclosed herein include as an essential component a volatile component that is preferably selected from the group consisting of a perfume, a fragrance, an insect repellent, a fumigant, a disinfectant, a bactericide, an insecticide, a pesticide, a germicide, an acaricide, a sterilizer, a deodorizer, a fogging agent and mixtures thereof. The concentration of volatile component in the multi-layer reaction mixture is from about 0.01% to about 20%, preferably from about 0.1% to about 15%, and more preferably from about 0.5% to about 10%, by weight, of the multi-layer reaction mixture.

"Volatile component" as used herein means any compound that is evolved from a multi-layer reaction mixture according to the present invention to the surrounding environment during an exothermic reaction. The term "volatile" does not imply any restrictions on the vapor pressure or the boiling point of the component. For example, many fine fragrances have boiling points well above the boiling point of water, while other fragrances have boiling points below water. Both types of fragrances fall within the definition of "volatile components" if they are evolved during an exothermic reaction according to the present invention. Having said that, it is often desirable, although by no means required, that the volatile component have a boiling point that is at least about 30° C. lower than the boiling point of the aqueous solution Necessarily, however, the aqueous solution cannot be considered the volatile component even though a portion of the aqueous solution may evolve during the exothermic reaction.

Fragrances are preferred volatile components for use in the present multi-layer reaction mixture and preferred fragrances are selected from the group consisting of musk oil, civet, castreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, cauout oil, salvia oil, clove oil, chamomille oil, sandalwood oil, costus oil, labdanum oil, broom extract, carrot seed extract, jasmine extract, minmosa extract, narcissus extract, olibanum, extract, rose extract, acetophenonene, dimethylinadane derivatives, naphthaline derivatives, allyl caprate, .alpha.-amylcinnamic aldehyde, anethole, anisaldehyde, benzyl acetate, benzyl alcohol, benzyl propionate, borneol, cinnamyl acetate, cinnamyl alcohol, citral citronnellal, cumin aldehyde, cyclamen aldehyde, decanol, ethyl butyrate, ethyl caprate, ethyl cinnamate, ethyl vanillin, eugenol, geraniol, exenol, alpha.-hexylcinnamic aldehyde, hydroxycitrolnellal, indole, iso-amyl acetate, iso-amyl iso-valeratek iso-eugenol, linalol, linalyl acetate, p-methylacetophenone, methyl anthranilate, methyl dihydroasmonate, methyl eugenol, methyl-.beta.-naphthol ketone, methylphenhlcarbinyl acetate, musk ketol, musk xylol, 2,5,6-nanodinol, .gamma.-nanolactone, phenylacetoaldehydodimethyl acetate, beta.-phenylethyl alcohol, 3,3,5-trimethylcyclohexanol, .gamma.-undecalactone, undecenal, vanillin, and mixtures thereof.

Aqueous Solution

An optional component of the present reaction mixtures is an aqueous solution. The aqueous solution performs two functions in the reaction mixture. Specifically, it dissolves the water soluble coating on the exothermic particles and then reacts with the exothermic generating particles to generate heat. It is understood that the amount of the aqueous solution is quite flexible. While a sufficient amount of the aqueous solution must be present to dissolve the coating and to react with the exothermic particles, excess aqueous solution is often acceptable and may even be desirable. In fact, excess aqueous solution acts as a heat sink for the reaction system. In this capacity the aqueous solution can, in some circumstances, be used to control the maximum temperature of a given reaction system. The aqueous solution, however, is generally not useful for controlling the time verses temperature curves for the reaction system as described above. Thus, those skilled in the art will be able to select the proper amount of aqueous solution for a given reaction system.

The most common and most preferred aqueous solution is water and solutions containing water. Monohydric alcohols and other low molecular weight liquids are suitable for use in the present invention. The only criteria for an "aqueous solution" is that it dissolve the water soluble coatings described above, and that it react with the chosen exothermic generating particles. The concentration of aqueous solution in the multi-layer reaction mixture is from about 30% to about 97%, preferably from about 50% to about 95%, and more preferably from about 60% to about 90%, by weight, of the multi-layer reaction mixture.

Buffer

The multi-layer reaction mixtures of the present invention will often include, as an option component, a buffer. The buffer, if present at all, need not be in all of the layers. The buffer can provide a variety of benefits, such as acceleration or deceleration of the exothermic reaction, and pH control at the end of the reaction. It is well known that certain exothermic generating particles will react faster than others. A buffer can speed up or slow down a reaction mixture. It is understood, however, that even with a buffer, uncontrolled exothermic reactions will generally follow the time vs. temperature curves depicted in Lines "A" and "a" of FIGS. 3 and 4. Thus, the buffer works to provide a favorable thermodynamic environment for the reaction mixture, but the buffer does not control the time vs. temperature profile of the reaction. With regard to pH, it is often desirable to control the pH both during the reaction and at the end of the reaction. During the reaction, the pH can contribute to the favorable thermodynamic environment as discussed above, and it can regulate the final pH of the reaction mixture when the exothermic reaction is nearing completion. The final pH may be important because at certain pHs the reaction products will precipitate leaving a relatively clear solution. The clear solution may be desirable and it can signal the end of the reaction. Regardless, a buffer may help the formulator of the multi-layer reaction mixtures disclosed herein.

Preferably, if a buffer is present in the multi-layer reaction mixtures of this invention, the ratio by weight of the exothermic generating particles to the buffer is in the range of from 1000:1 to 1:1000, preferably from 500:1 to 1:500, and more preferably from 200:1 to 1:200. And the buffer is preferably selected from the group consisting of citric acid, malic, acid, fumaric acid, succinic acid, tartaric acid, formic acid, acetic acid, propanoic acid, butyric acid, valeric acid, oxalic acid, malonic acid, glutaric acid, adipic acid, glycolic acid, aspartic acid, pimelic acid, maleic acid, phthalic acid, isophthalic acid, terphthalic acid, glutamic acid, lactic acid, hydroxyl acrylic acid, alpha hydroxyl butyric acid, glyceric acid, tartronic acid, salicylic acid, gallic acid, mandelic acid, tropic acid, ascorbic acid, gluconic acid, cinnamic acid, benzoic acid, phenylacetic acid, nicotinic acid, kainic acid, sorbic acid, pyrrolidone carboxylic acid, trimellitic acid, benzene sulfonic acid, toluene sulfonic acid, potassium dihydrogen phosphate, sodium hydrogen sulfite, sodium dihydrogen phosphate, potassium hydrogen sulfite, sodium hydrogen pyrosulfite, acidic sodium hexametaphosphate, acidic sodium pyrophosphate, acidic potassium pyrophosphate, sulfamic acid, ortho-phosphoric acid, pyro-phosphoric acid and mixtures thereof.

Other Ingredients

The multi-layer reaction mixtures of the present invention may comprise, as optional components, other ingredients. These optional ingredients can be, for example, visual enhancement agents selected from the group consisting of a dye, a chemiluminescence agent, a fluorescence agent, a pearlescence agent, and mixtures thereof. More preferably, the visual enhancement agent is selected from the group consisting of fire-fly luciferase, adenosinetriphosphate, ethylene glycol disteacate and mixtures thereof. These visual enhancement agents can be used to color the multi-layer reaction mixture, make it "glow", or provide other visually satisfying effects. The concentration of in the other ingredients, if present in the multi-layer reaction mixture is from about 0.01% to about 30%, preferably from about 0.1% to about 20%, and more preferably from about 0.5% to about 15%, by weight, of the multi-layer reaction mixture.

Apparatus

In yet another aspect of this invention there is provided an apparatus for generating heat, the apparatus comprises a container and a multi-layered reaction mixture comprising the following reaction components: exothermic generating particles comprising a water soluble coating that encases a portion of the particles; a volatile component; and an aqueous solution. The apparatus optionally further comprises a buffer. The reaction components for use in the apparatuses of the present invention are the same as those discussed above. The apparatus of the present invention is preferably a self contained and portable device in which an exothermic reaction is conducted. Preferably, the apparatus container should have at least one vent or opening to emit the volatile components that are evolved during the exothermic reaction. Moreover, the container should be constructed of a material that can withstand the maximum temperature of the exothermic reaction. Many materials fulfill this requirement because the maximum temperature of the reaction might be as low as 35° C., higher temperature reaction might require higher temperature tolerance. Glass, plastic, styrofoam, metal, liquid impermeable paper, and many other materials are suitable for use in the present invention. The container is preferably clear, transparent, or translucent, although opaque containers, while less preferable, are suitable for use herein. In the present apparatuses, the exothermic generating particles can be in the form of a dry powder, suspended in a homogenous gel, or suspended in a non-aqueous solution.

The multi-layer reaction mixture used in the apparatuses of the present invention should be controllable as discussed above. That is, when the reaction components are mixed together in the present apparatuses, the multi-layer reaction mixture should increase in temperature to a Set Temperature that is greater than about 35° C. and less than about 75° C., preferably between about 35° C. and 60° C., and most preferably between about 35° C. and 50° C., within less than about 20 minutes, preferably within less than about 10 minutes and more preferably within less than about 5 minutes. Preferably, the multi-layer reaction mixture within the apparatus remains within 15° C. of the Set Temperature for at least about 45 minutes, preferably at least about 60 minutes, and more preferably at least about 90 minutes. Other control sequences, such as those describe above in conjunction with the multi-layer reaction mixture are contemplated for use in the present apparatus.

In one preferred embodiment of the present invention, the apparatus includes a light source. The light source, which can optionally provide colored light, can be used to enhance the visual effect of the apparatus. Moreover, as discussed above, visual enhancement agents may be employed in the multi-layer reaction mixture in addition to the light source. The light source can be used to accentuate the visual enhancement agents, or simply to "light up" the apparatus. The light source can be battery powered, solar powered or the like. While generally not preferred, the light source could be externally powered by, for example, an electrical outlet. The apparatuses of the present invention are preferably portable, thus using external power may limit the portability. The light source can be within the container, or adjacent the exterior of the container. If the light source is placed in the container, it will be preferable to encase the light source and its power supply in a liquid impermeable barrier to shield the device from the aqueous solution.

The light source may contribute some heat to the multi-layer reaction mixture, but that is not the desired function. Moreover, most battery operated devices operated at low voltage, and produce very little heat. Thus, the light source is not intended to function as a control mechanism even though it may add additional heat to the reaction system.

One especially preferred light source for use in the present apparatuses is a light emitting diode ("LED"). LEDs are well known to the art and examples of these devices can be found in, for example, U.S. Pat. No. 5,963,185, which issued to Havel on Oct. 5, 1999, and U.S. Pat. No. 5,940,683, which issued to Holm et al. on Aug. 17, 1999. The entire disclosure of the Havel and Holm et al. patents are incorporated herein by reference. LEDs are small devices that provide numerous colors from a single source. Thus, from one device, a variety of colors can be projected onto the reaction mixture increasing the range of available visual effects. These devices have the additional benefit in that they operate at low power, and would require only a small battery or solar power cell.

EXAMPLES

The following examples illustrate the multi-layer reaction mixtures of the present invention, but are not necessarily meant to limit or otherwise define the scope of the invention.

Method of Coating the Exothermic Generating Particles

Exothermic generating particles are coated with polyethylene glycol as follows. A premix is made by combining magnesium powder and anhydrous citric acid (1:6.5 w/w, both components from Wako Chemicals), and then a fragrant oil is added to this premix. The premix is then added into melted polyethylene glycol. The meted polyethylene is a mixture of three different molecular weights, PEG 600 (from Union Carbide), PEG 1000 (from Wako Chemicals), and PEG 2000 (from Wako Chemicals). The melted PEG mixture is around 50° C. The mixture is then cooled at 5° C. for 10 min to approximate 20–25° C. The product comprises PEG of three different molecular weights, a fragrant oil, magnesium powder and anhydrous citric acid powder, and is a gel with suspended particles.

What is claimed is:

1. A multi-layer reaction mixture, comprising the following reaction components:
   a) exothermic generating particles comprising a water soluble coating that encases a portion of the particles; and
   b) a volatile component;
wherein at least two layers of the reaction mixture comprise exothermic generating particles and wherein at least one layer of the reaction mixture comprises a portion of the exothermic generating particles suspended in a gel comprising the water soluble coating.

2. The multi-layer reaction mixture of claim 1, wherein the reaction components further comprise additional reactants selected from the group consisting of a buffer, an aqueous solution, and mixtures thereof.

3. The multi-layer reaction mixture of claim 1, wherein, when the reaction components are mixed with an aqueous solution, the resulting reaction mixture is operable to increase in temperature to a Set Temperature that is greater than about 35° C. and less than about 75° C., within less than about 20 minutes.

4. The multi-layer reaction mixture of claim 3, wherein the resulting reaction mixture is operable to remain within 15° C. of the Set Temperature for at least about 45 minutes.

5. The multi-layer reaction mixture of claim 1, wherein the volatile component is selected from the group consisting of a perfume, a fragrance, an insect repellent, a fumigant, a disinfectant, a bactericide, an insecticide, a pesticide, a germicide, an acaricide, a sterilizer, a deodorizer, a fogging agent and mixtures thereof.

6. The multi-layer reaction mixture of claim 1, wherein the volatile component is selected from the group consisting of a musk oil, civet, castreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, cauout oil, salvia oil, clove oil, chamomille oil, sandalwood oil, costus oil, labdanum oil, broom extract, carrot seed extract, jasmine extract, minmosa extract, narcissus extract, olibanum, extract, rose extract, acetophenonene, dimethylinadane derivatives, naphthaline derivatives, allyl caprate, .alpha.-amylcinnamic aldehyde, anethole, anisaldehyde, benzyl acetate, benzyl alcohol, benzyl propionate, borneol, cinnamyl acetate, cinnamyl alcohol, citral citronnellal, cumin aldehyde, cyclamen aldehyde, decanol, ethyl butyrate, ethyl caprate, ethyl cinnamate, ethyl vanillin, eugenol, geraniol, exenol, alpha.-hexylcinnamic aldehyde, hydroxycitrolnellal, indole, iso-amyl acetate, iso-amyl iso-valeratek iso-eugenol, linalol, linalyl acetate, p-methylacetophenone, methyl anthranilate, methyl dihydroasmonate, methyl eugenol, methyl-.beta.-naphthol ketone, methylphenhlcarbinyl acetate, musk ketol, musk xylol, 2,5,6-nanodinol, .gamma.-nanolactone, phenylacetoaldehydodimethyl acetate, beta.-phenylethyl alcohol, 3,3,5-trimethylcyclohexanol, .gamma.-undecalactone, undecenal, vanillin, and mixtures thereof.

7. The multi-layer reaction mixture of claim 1, wherein the exothermic generating particles are selected from the group consisting of uncomplexed metals, metal salts, metal oxides, metal hydroxides, metal hydrides and mixtures thereof, wherein the metals are selected from the group consisting of beryllium, magnesium, lithium, sodium, calcium, potassium, iron, copper, zinc, aluminum and mixtures thereof.

8. The multi-layer reaction mixture of claim 1, wherein the exothermic generating particles have an average particle diameter of from about 10 microns to about 1000 microns.

9. The multi-layer reaction mixture of claim 7, wherein the exothermic generating particles are selected from the group consisting of beryllium hydroxide, beryllium oxide, beryllium oxide monohydrate, lithium aluminum hydride, calcium oxide, calcium hydride, potassium oxide, magnesium chloride, magnesium sulfate, aluminum bromide, aluminum iodide, sodium tetraborate, sodium phosphate and mixtures thereof.

10. The multi-layer reaction mixture of claim 1, wherein the water soluble coating comprises a water soluble material selected from the group consisting of natural water-soluble polymers, inorganic water-soluble polymers, synthetic water-soluble polymers, semi-synthetic water-soluble polymers, polymers of plant origin, polymers of microorganism origin, polymers of animal origin, starch polymers, cellulose polymers, alginate polymers, vinyl polymers, polyoxyethylene polymers, acrylate polymers, and mixtures thereof.

11. The multi-layer reaction mixture of claim 1, wherein the water soluble coating comprises a water soluble material selected from the group consisting of gum arabic, gum tragacanth, galactan, gum guar, carob-seed gum, karaya gum, carrageenan, pectin, agar, quince seed, alge-colloid, starch, glycyrrhizic acid, gum xanthan, dextran, succin-glucane, pullulan, collagen, casein, albumin, gelatin, carboxy-methyl starch, methyl-hydroxypropyl starch, methyl-cellulose, nitro-cellulose, ethyl-cellulose, methyl-hydroxypropyl-cellulose, hydroxy-ethyl-cellulose, sodium cellulose sulfate, hydroxypropyl-cellulose, sodium carboxy-methyl-cellulose, crystalline cellulose, cellulose powder, sodium alginate, propylene glycol alginate ether, polyvinyl alcohol, poly (vinyl methyl ether), poly-vinyl-pyrrolidone, carboxy-vinyl polymers, alkyl co-polymers of acrylic acid and methacrylic acid, polyethylene glycol having a molecular weight between 200 and 100,000, co-polymers of polyoxy-ethylene and polyoxy-propylene, sodium poly-acrylate, poly ethylacrylate, poly acrylamide, polyethylene imine, cation polymers, bentonite, aluminum magnesium silicate, hectorite, silicic anhydride, and mixtures thereof.

12. The multi-layer reaction mixture of claim 1, wherein the water soluble coating comprises a material selected from the group consisting of water-soluble alkylene glycols, water-soluble alcohols, and mixtures thereof.

13. The multi-layer reaction mixture of claim 1, wherein, when the reaction components are mixed with an aciueous solution, the resulting reaction mixture is operable to increase in temperature at an actual rate of increase that is measured in ° C./minute, and the actual rate of increase remains within 0.5° C./minute of a predetermined rate of increase for at least about 45 minutes.

14. The multi-layer reaction mixture of claim 1, wherein, when the reaction components are mixed with an aqueous solution, the resulting reaction mixture is operable to increase in temperature to a First Set Temperature and remain within 15° C., preferably within 10° C., and more preferably within 5° C., of the First Set Temperature for a first period of time and then change to a Second Set Temperature and remain within 15° C., preferably within 10° C., and more preferably within 5° C., of the Second Set Temperature for a second period of time.

15. The multi-layer reaction mixture of claim 1, further comprising a layer that is substantially free of exothermic generating particles.

16. The multi-layer reaction mixture of claim 1, wherein the water soluble coating comprises polyethylene glycol having a molecular weight between 600 and 20,000.

17. The multi-layer reaction mixture of claim 1, wherein the exothermic generating particles have an average particle diameter of from about 100 microns to about 500 microns.

18. The multi-layer reaction mixture of claim 1, wherein the exothermic generating particles have an average particle diameter of from about 200 microns to about 400 microns.

19. A multi-layer reaction mixture, comprising the following reaction components:
   a) exothermic generating particles comprising a water soluble coating that encases a portion of the particles; and
   b) a volatile component,
wherein at least two layers of the reaction mixture comprise exothermic generating particles suspended in a gel comprising the water soluble coating.

20. The multi-layer mixture of claim 19, wherein at least one layer of the reaction mixture is substantially free of exothermic generating particles.

21. The multi-layer mixture of claim 20, wherein at least one layer of the multi-layer reaction mixture comprises exothermic generating particles with essentially no coating thereon.

* * * * *